(12) United States Patent
Hagino et al.

(10) Patent No.: US 8,299,447 B2
(45) Date of Patent: Oct. 30, 2012

(54) ROTATING IRRADIATION APPARATUS

(75) Inventors: Takeshi Hagino, Chiyoda-ku (JP);
Hiroshi Otani, Chiyoda-ku (JP)

(73) Assignee: Mitsubishi Electric Corporation,
Chiyoda-Ku, Tokyo (JP)

( * ) Notice: Subject to any disclaimer, the term of this patent is extended or adjusted under 35 U.S.C. 154(b) by 49 days.

(21) Appl. No.: 12/936,622

(22) PCT Filed: Jun. 18, 2008

(86) PCT No.: PCT/JP2008/061127
§ 371 (c)(1),
(2), (4) Date: Oct. 6, 2010

(87) PCT Pub. No.: WO2009/153864
PCT Pub. Date: Dec. 23, 2009

(65) Prior Publication Data
US 2011/0024645 A1   Feb. 3, 2011

(51) Int. Cl.
*A61N 5/00* (2006.01)
(52) U.S. Cl. .................................. 250/492.1; 607/88
(58) Field of Classification Search .............. 250/491.1, 250/492.1, 492.21, 492.3, 396 R; 600/2, 600/472; 607/88
See application file for complete search history.

(56) References Cited

U.S. PATENT DOCUMENTS

| | | | | |
|---|---|---|---|---|
| 4,641,104 A * | 2/1987 | Blosser et al. | ................. | 315/502 |
| 5,993,373 A * | 11/1999 | Nonaka et al. | .................... | 600/1 |
| 7,875,861 B2 * | 1/2011 | Huttenberger et al. | .... | 250/491.1 |
| 7,939,809 B2 * | 5/2011 | Balakin | ..................... | 250/396 R |
| 2004/0111134 A1 * | 6/2004 | Muramatsu et al. | ............ | 607/88 |
| 2004/0183035 A1 * | 9/2004 | Yanagisawa et al. | ...... | 250/492.3 |
| 2007/0217575 A1 * | 9/2007 | Kaiser et al. | .................. | 378/209 |
| 2008/0179544 A1 * | 7/2008 | Kaiser et al. | ............... | 250/492.1 |

(Continued)

FOREIGN PATENT DOCUMENTS

JP            11-047287 A       2/1999
(Continued)

OTHER PUBLICATIONS

International Search Report (PCT/ISA/210) issued on Sep. 9, 2008, by Japanese Patent Office as the International Searching Authority for International Application No. PCT/JP2008/061127.

*Primary Examiner* — Robert Kim
*Assistant Examiner* — Jason McCormack
(74) *Attorney, Agent, or Firm* — Buchanan Ingersoll & Rooney PC

(57) ABSTRACT

There is provided a rotating irradiation apparatus that can secure as large an access floor as possible, reduce noise during the formation of an access floor, and stably operate with a simple structure. The rotating irradiation apparatus includes an irradiation device 7 that irradiates a charged particle beam, a frame 1 on which the irradiation device is mounted and which rotates the irradiation device so that a patient lying on a treatment table 8 fixed to a stationary floor surface is irradiated with the charged particle beam, a ring 10 that is rotatably held on an inner periphery of the frame, an opening/closing-type floor 20 which is provided inside the ring and of which a portion through which the irradiation device passes is openable and closable, and drive means 28 that reversely rotates the ring in synchronization with the rotation of the irradiation device so as to maintain the opening/closing-type floor horizontal.

6 Claims, 11 Drawing Sheets

U.S. PATENT DOCUMENTS

2009/0304153 A1* 12/2009 Amelia et al. .................. 378/65
2011/0313232 A1* 12/2011 Balakin ............................ 600/1

FOREIGN PATENT DOCUMENTS

| | | |
|---|---|---|
| JP | 2001-129103 A | 5/2001 |
| JP | 2001-259058 A | 9/2001 |
| JP | 2001-321453 A | 11/2001 |
| JP | 2004-121309 A | 4/2004 |
| JP | 2007-195877 A | 8/2007 |
| WO | WO 2006060886 A1 * | 6/2006 |

* cited by examiner

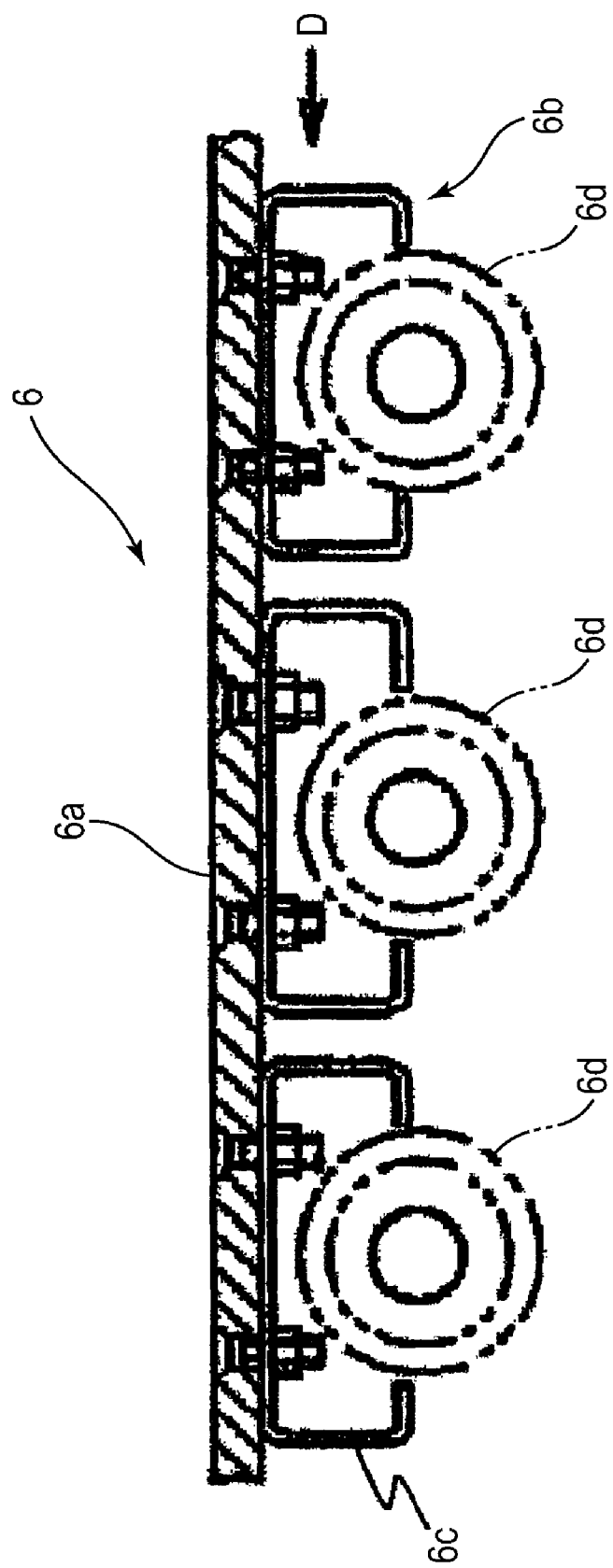

ROTATING IRRADIATION APPARATUS

TECHNICAL FIELD

The present invention relates to a rotating irradiation apparatus including a charged particle beam irradiation section that is rotated around a patient in a radiation therapy apparatus or the like used for a cancer treatment.

BACKGROUND ART

In recent years, a cancer treatment apparatus using protons or heavy ions has been developed and constructed as a radiation therapy apparatus that is intended for cancer treatment. As known well, in a particle radiation therapy that uses protons, heavy ions, or the like, it may be possible to intensively irradiate a cancer-affected area as compared to radiation therapy in the related art that uses X-rays, gamma rays, or the like, and to treat the cancer-affected region without affecting healthy cells.

A particle radiation therapy apparatus is generally provided with a rotating irradiation device (rotating gantry) in order to irradiate a patient in an arbitrary direction. The rotating gantry is adapted so as to irradiate a patient with a charged particle beam at an arbitrary rotation angle by rotating a particle beam irradiation unit through 360° of rotation.

If the rotating gantry is adapted so as to irradiate a patient with a charged particle beam at an arbitrary rotation angle by rotating a particle beam irradiation unit through 360° of rotation as described above, a treatment table to which the patient is fixed needs to be disposed on a stationary side (building) relative to the rotation and the treatment table is formed to protrude from the stationary side. Accordingly, an access floor (hereinafter, referred to as a movable floor), which is always maintained horizontal regardless of the rotation angle of the rotating gantry, is required so that a doctor, a radiation technologist, or the like, who performs the treatment, can always work while being close to the patient.

For example, FIGS. 10 and 11 show the structure of a device in the related art that is disclosed in Patent Citation 1. FIG. 10 is a cross-sectional view showing the main parts of a rotating gantry. Reference numeral 1 denotes a rotating irradiation chamber for particle radiation therapy, reference numeral 2 denotes a stationary body, reference numeral 2a denotes a guide rail of the stationary body (for a movable floor), reference numeral 2b denotes a guide rail (for a treatment bed), reference numeral 3 denotes a particle beam irradiation unit, reference numeral 4 denotes a rotating body, reference numeral 4a denotes a rotating body supporting ring, reference numeral 4b denotes a support roller, reference numeral 5 denotes a guide rail supporting body, reference numeral 5a denotes a guide rail of the rotating body (for a movable floor), reference numeral 5b denotes a guide rail supporting body supporting member, reference numeral 5c denotes supporting rollers, reference numeral 5d denotes engaging holes, reference numeral 6 denotes a movable floor, reference numeral 7 denotes rod actuating electric cylinders, and reference numeral 7a denotes locking rods. FIG. 11 is an enlarged cross-sectional view of a movable floor unit. Reference numeral 6a denotes a rubber belt, reference numeral 6b denotes a carrier, reference numeral 6c denotes a beam member, and reference numeral 6d denotes guide rollers.

The movable floor 6 includes a rubber belt 6a, a carrier 6b, a beam member 6c, and guide rollers 6d, and is formed in an endless curved shape so that the rotating gantry forms a horizontal movable floor below a treatment bed regardless of the rotation of the rotating body 4 and the particle beam irradiation unit 3. The movable floor 6 forms an access floor by being guided by the guide rail 2a of the stationary body and the guide rail 5a of the rotating body and rolling in the guide rail as the particle beam irradiation unit 3 is rotated. The guide rail supporting body 5 provided with the guide rail 5a of the rotating body is provided inside the rotating body 4 with the supporting rollers 5c interposed therebetween, and the rod actuating electric cylinders 7 for the actuating locking rods 7a are provided above the stationary body 2 provided with the stationary guide rail 2a. The locking rods 7a are formed so as to be inserted into the engaging holes 5d that are formed at the guide rail supporting body supporting member 5b for supporting the supporting rollers 5c. Accordingly, even though the rotating body 4 and the particle beam irradiation unit 3 are rotated and the movable floor 6 is moved in synchronization with the rotation of the rotating body and the particle beam irradiation unit, it may be possible to stop the guide rail supporting body 5. Therefore, it may be possible to continue to maintain the lower portion of the movable floor 6 horizontal.

Patent Citation 1: JP-A-2001-129103

DISCLOSURE OF INVENTION

Problems that the Invention is to Solve

However, in the above-mentioned structure, it is necessary to precisely machine the guide rail 5a of the rotating body and the guide rail 2a of the stationary body, which supports the movable floor 6, or to form the movable floor 6 across the entire drive range of the particle beam irradiation unit 3. Since the rod actuating cylinders 7 for stopping the guide rail supporting body 5 need to be installed on the stationary side, there are problems in that the size of the structure is large and manufacturing costs are increased.

Further, there is a problem in that noise is generated when guide rollers 6d provided on the movable floor 6 roll in the guide rail 5a of the rotating body and the guide rail 2a of the stationary body. This noise tends to be largely generated at the boundary between the arc and the horizontal portion of the guide rail.

The invention has been made to solve the above-mentioned problems, and an object of the invention is to provide a rotating gantry that can simplify the structure for forming a movable floor and reduce noise during the formation of a movable floor.

Means for Solving the Problems

An rotating irradiation apparatus according to the invention includes an irradiation device that irradiates a charged particle beam, a frame on which the irradiation device is mounted and which rotates the irradiation device so that a patient lying on a treatment table fixed to a stationary floor surface is irradiated with the charged particle beam, a ring that is rotatably held on an inner periphery of the frame, an opening/closing-type floor which is provided inside the ring and of which a portion through which the irradiation device passes is openable and closable, and drive means that reversely rotates the ring in synchronization with the rotation of the irradiation device so as to maintain the opening/closing-type floor horizontal.

Advantageous Effects of the Invention

According to the invention, the opening/closing-type floor is combined with drive means that reversely rotates the ring in synchronization with the rotation of the irradiation device so as to maintain the opening/closing-type floor horizontal. Accordingly, it may be possible to obtain a rotating irradiation apparatus that can secure as large an access floor as possible, reduce noise during the formation of an access floor, and stably operate with a simple structure.

BRIEF DESCRIPTION OF DRAWINGS

FIG. 11 is an enlarged view of a movable floor unit in the related art.

EXPLANATION OF REFERENCES

Figure 1B:
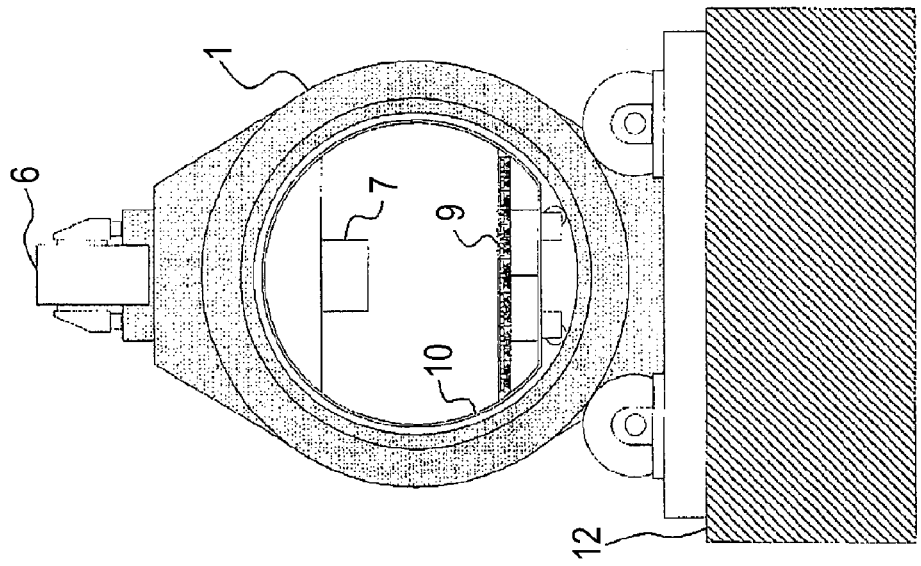
FIG. 1 is a cross-sectional view showing the main parts of a rotating irradiation apparatus according to a first embodiment of the invention.

1: frame
2: rotating ring
3: gantry rotating drive device
4: brake device
5: cable spool
6: beam transport device
7: irradiation device
8: treatment table
9: opening/closing mechanism
10: ring
11: treatment table base
12: building
20: opening/closing-type floor
22: slide rail
23: base
24: air cylinder
25: roller
26: guide ring
27: guide rail
28: drive motor

BEST MODE FOR CARRYING OUT THE INVENTION

First Embodiment

Figure 1A:
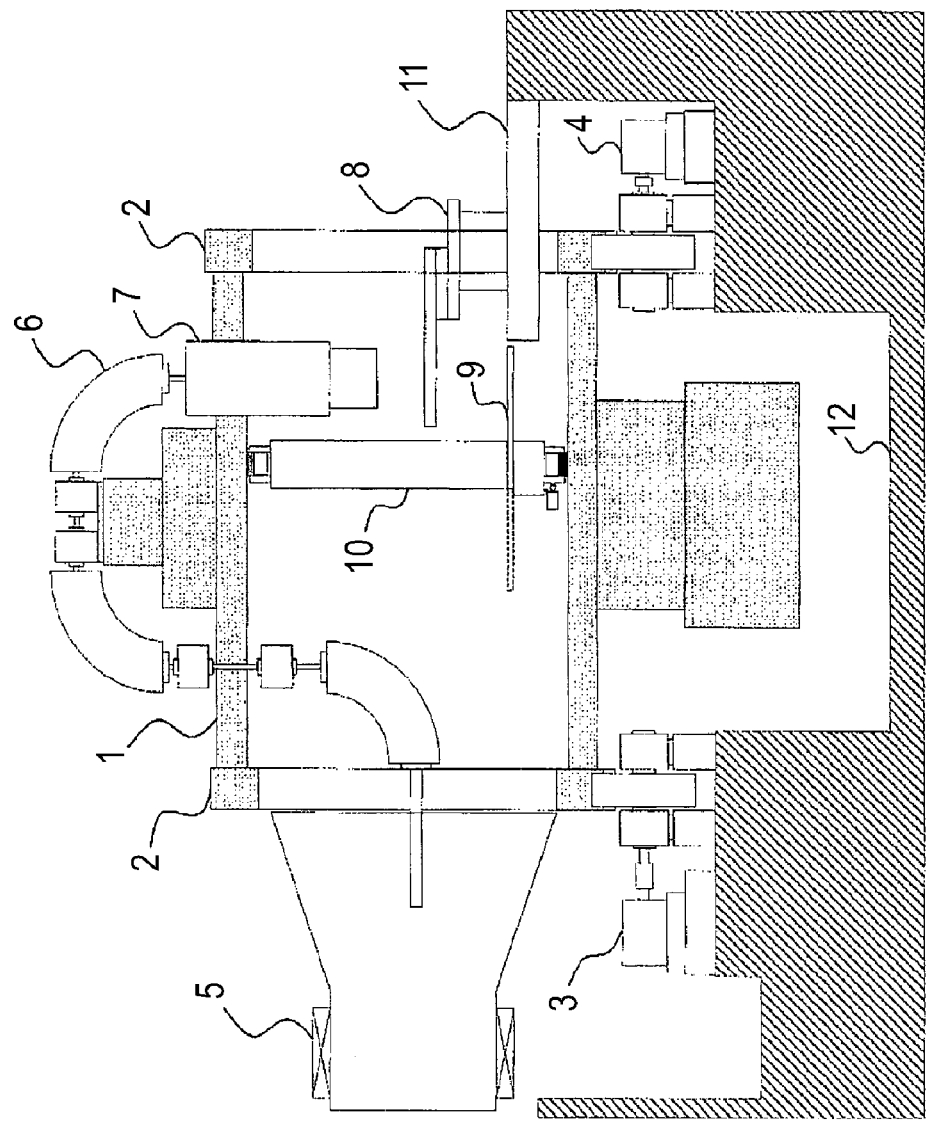
Figure 2:
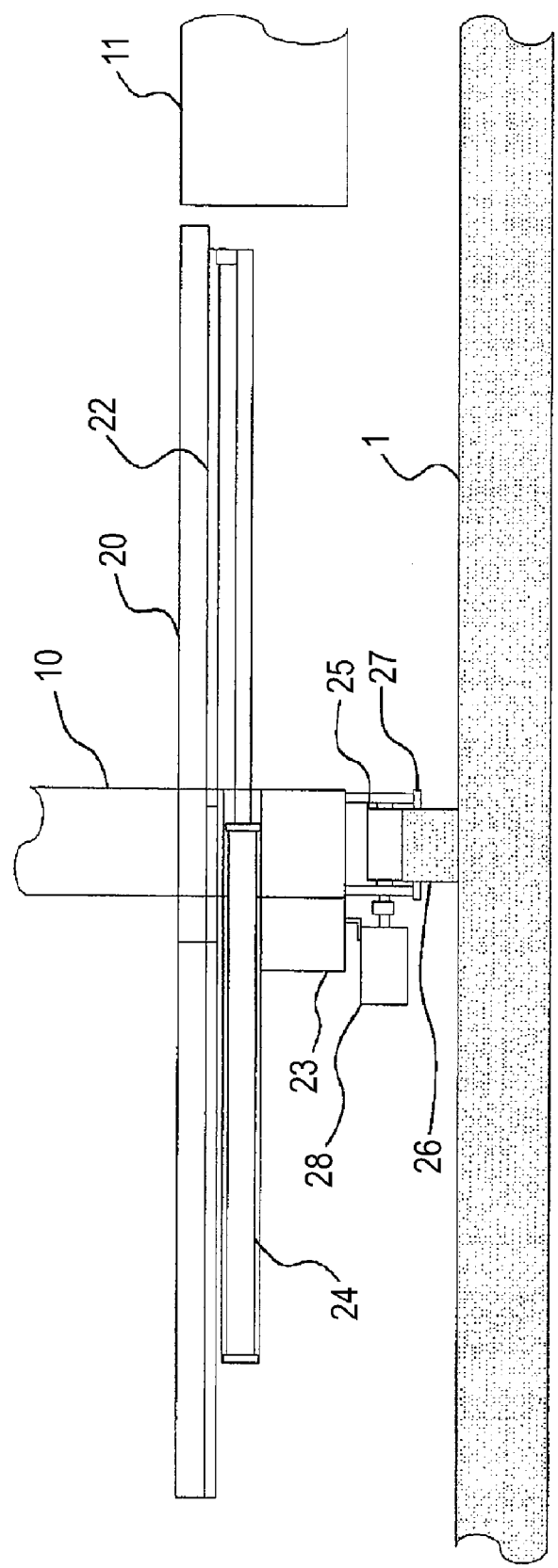
FIG. 2 is a side view of an opening/closing mechanism of an opening/closing-type floor according to a first embodiment of the invention.
Figure 3:
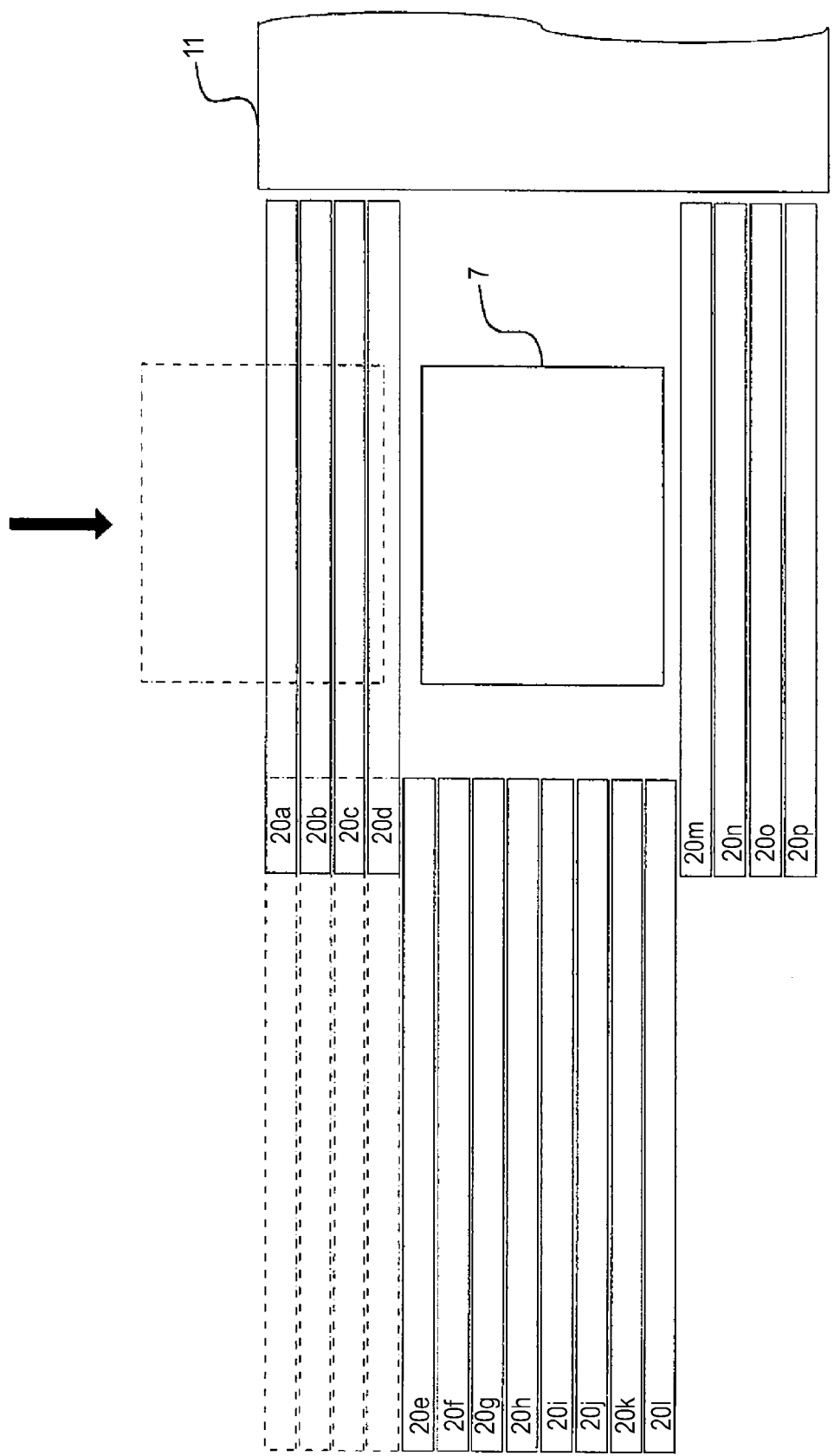
FIG. 3 is a top view of the opening/closing-type floor according to the first embodiment of the invention.

A first embodiment of the invention will be described below with reference to FIGS. 1 to 3. FIGS. 1 to 3 are views showing a rotating irradiation apparatus according to a first embodiment, FIG. 1A is a side cross-sectional view of the entire rotating gantry taken along a rotation axis of a rotating gantry, and FIG. 1B is a front view of the rotating gantry when observed in a direction perpendicular to the rotation axis. FIG. 2 is a side view of an opening/closing mechanism of an opening/closing-type floor, and FIG. 3 is a top view of the slide opening/closing-type floor.

In FIG. 1, reference numeral 1 denotes a frame of a rotating gantry, reference numeral 2 denotes a rotating ring that is provided on the frame, reference numeral 3 denotes a gantry rotating drive device that is provided with a roller receiving rotating ring 2 and a motor to be rotationally driven or a reduction gear, reference numeral 4 denotes a brake device that is provided with a ring receiving the rotating ring 2 and a brake or a reduction gear, reference numeral 5 denotes a cable spool that supplies a wire and a pipe into a rotating gantry to be rotated through 360° of rotation, reference numeral 6 denotes a beam transport device that transports a charged particle beam introduced into the rotating gantry, and reference numeral 7 denotes an irradiation device that shapes a transported charged particle beam so as to correspond to a patient's affected area to be irradiated and irradiates the patient's affected area with the shaped charged particle beam.

Reference numeral 8 denotes a treatment table on which a patient gets, reference numeral 9 denotes an opening/closing mechanism that opens and closes an opening/closing-type floor corresponding to a portion through which the irradiation device 7 passes, reference numeral 10 denotes a ring which is rotatably supported in the frame 1 and where the opening/closing mechanism 9 is provided, reference numeral 11 denotes a treatment table base where the treatment table 8 is installed, and reference numeral 12 denotes a building. Meanwhile, the treatment table base 11 is a stationary floor.

In FIG. 2, reference numeral 20 denotes a slide opening/closing-type floor corresponding to the opening/closing mechanism 9, reference numeral 22 denotes slide rails that are mounted on opening/closing-type floor 20, reference numeral 23 denotes a base that is provided inside ring 10, reference numeral 24 denotes an air cylinder that is a drive mechanism for making the opening/closing-type floor slide, reference numeral 25 denotes rollers that are provided on the base 23 and roll inside a guide ring 26 mounted on the frame 1, reference numeral 26 denotes a guide ring that guides the rollers 25 provided on the base 23, reference numeral 27 denotes guide rails that restrict and guide the movement and inclination of the opening/closing mechanism 9 and the ring 10 in the thrust direction (a direction of the rotation axis), and reference numeral 28 denotes drive motors that reversely rotate the rollers 25 in synchronization with the rotation of the guide ring 26 and the base 23.

FIG. 3 is a top view of the opening/closing-type floor. The opening/closing-type floor 20 is segmented into a plurality of floors 20a to 20p, and the respective segmented floors are formed so as to slide. The respective segmented floors are translated in the horizontal plane by the opening/closing mechanism 9 along the floor surface that is the upper surface of the opening/closing-type floor, and form a horizontal floor surface.

Next, operation will be described. The charged particle beam, which is introduced into the rotating gantry in FIG. 1, is transported to the irradiation device 7 by the beam transport device 6 that is formed of a deflection electromagnet, a quadrupole electromagnet, or the like. The irradiation device 7 irradiates the patient's affected area with the charged particle beam after shaping the charged particle beam so as to correspond to the shape of the patient's affected area to be irradiated.

The patient is fixed and positioned on the treatment table 8, and a predetermined affected area to be irradiated is irradiated with a charged particle beam. Since the treatment table 8 needs to be operated so that the patient's affected area to be irradiated corresponds to an isocenter, that is, an irradiation position, the treatment table may perform multi-axis positioning operations, such as up-down left-right operation, forward-backward operation, and rotation. The rotating gantry allows the patient to be irradiated with a beam in any of 360° of direction by the rotating beam transport device 6 and the irradiation device 7 in addition to the multi-axis positioning operations of the treatment table, and the patient may be irradiated with a beam in various directions while the patient looks up. This is the same as in the related art.

The characteristics of the rotating gantry of the invention are the simplification of the structure of the opening/closing mechanism 9 for opening and closing a portion of the floor through which the irradiation device 7 passes when reaching a position below the patient. The characteristics will be described with reference to FIGS. 1 to 3. The Opening/closing-type floor 20 slides in a horizontal direction by the air cylinder 24, and the opening/closing-type floor 20 may form an access floor accessing to the treatment table 8 when being closed.

The base 23 on which the opening/closing-type floor 20, the air cylinder 24, and the like are mounted applies a load to the inner surface of the rotating gantry by the rollers 25. The opening/closing mechanism 9 should be maintained horizontal regardless of the rotation of the rotating gantry in order to always form a horizontally movable floor by the opening/closing-type floor 20. Even though the rotating gantry is rotated, the entire opening/closing mechanism 9 may be horizontally positioned at the lowest portion in the rotating gantry so as to always correspond to the center of the inner surface of the frame 1 by controlling the drive motors 28 of the rollers 25 so that the rollers are reversely rotated in synchronization with the rotating gantry.

It may be possible to maintain the opening/closing mechanism 9 horizontal by performing feedback control using a servo motor or the like as the drive motor 28. In this structure that forms an access floor in the slidably movable floors, the opening/closing-type floor 20 may form a gap without being connected to the treatment table base 11 even when being closed. Even though the opening/closing mechanism 9 is slightly deviated from a horizontal position during the rotation of the rotating gantry, a problem such as the damage to the device does not occur. Slight time lag is generated in the feedback control using a servo motor or the like. However, if the opening/closing-type floor 20 is maintained horizontal during the stop of the rotating gantry, there is no problem. Accordingly, if slight inclination is allowed during the rotation, it may be possible to easily control the opening/closing mechanism 9 so that the opening/closing mechanism is reversely rotated in synchronization with the rotating gantry.

The guide rails 27 are provided so that the guide ring 26 provided in the frame 1 is interposed between the guide rails. Accordingly, when the rollers 25 are driven on the inner surface of the guide ring 26, the guide rails 27 restrict the position and inclination of the opening/closing-type floor 20 in the thrust direction.

The operation of the irradiation device 7 and the opening/closing-type floor 20 will be described below with reference to FIG. 3. The irradiation device 7 is rotated from a position, which is positioned immediately above the patient in the vertical direction, by an angle of ±180°. FIG. 3 shows that the irradiation device 7 is moved from the upper side of the drawing and is in a state corresponding to the maximum rotation stroke, that is, is positioned immediately below. The opening/closing-type floors 20a to 20l, which correspond to the portion through which the irradiation device 7 passes, are opened and secure the passage of the irradiation device 7. However, after the irradiation device 7 is completely positioned and stopped, the opening/closing-type floors 20a to 20d having formed the passage may be closed. Accordingly, the opening/closing-type floors corresponding to this portion are closed in order to secure as large an access floor as possible. If a portion of the opening/closing-type floor 20, which exists at positions corresponding to a passing path and a stop position of the irradiation device 7 and can be opened during the rotation (movement) of the rotating gantry and closed after the completion of the rotation (movement) as described above, are closed, it may be possible to secure as large an access floor as possible.

The number of the opening/closing-type floors 20 has been 16 in FIG. 3. However, if the opening/closing-type floor is further segmented, it may be possible to reduce the gap between the irradiation device 7 and the floor.

Floors, which are opened and closed so as to correspond to the position of the irradiation device 7 to be moved in this way, have been determined. Since the rotating gantry usually needs to be positioned with a fine accuracy of, for example, 0.1° and is controlled by a controller, such as a sequencer or a computer, it may be possible to facilitate the above-mentioned determination.

A portion of the opening/closing-type floor 20, which is opened before the rotation of the irradiation device 7 and closed after the completion of the rotation, has been closed as for the opening and closing of the opening/closing-type floor 20. However, even though the floors are opened and closed in synchronization with the position of the irradiation device 7, it may be possible to obtain the same advantages.

The opening/closing-type floor 20, which can be closed after the stop of the rotation, has been determined and closed. However, as long as the irradiation device 7 is formed not to be broken using the thrust force of the air cylinder 24, the opening/closing-type floor may be opened and closed by the following simple operation. That is, the entire opening/closing-type floor 20, which is opened making a passage, may be closed and the opening/closing-type floor 20, which exists at the position where irradiation device 7 is stopped and exists, may bump against the irradiation device 7 and stop.

As described above, a portion through which the irradiation device 7 passes has been formed of the segmented opening/closing-type floors 20 and the opening/closing-type floor 20 and the opening/closing mechanism 9 including the drive mechanism for driving the opening/closing-type floor have been received in the frame 1. Accordingly, it may be possible to prevent the interference between the treatment table 8 and the drive device for driving the treatment table, and to secure as large an access floor as possible with a simple structure.

Since the opening/closing-type floor 20, which is formed so as to slide by linear guides, is merely opened and closed by the air cylinder 24, it may be possible to create a comfortable environment where unnecessary noise is not generated and the patient does not feel uncomfortable. In the above-mentioned embodiment, there has been described a case where the opening/closing-type floor 20 is driven by using air cylinder 24. However, the opening/closing-type floor may be driven by mechanisms, such as a hydraulic cylinder, a motor cylinder, a motor and a ball screw, or a motor and a chain, or the drive method using them.

As described above, the rotating irradiation apparatus according to the first embodiment includes the irradiation device 7 that irradiates a charged particle beam; the frame 1 on which the irradiation device is mounted and which rotates the irradiation device so that a patient lying on the treatment table 8 fixed to the stationary floor surface is irradiated with the charged particle beam; the ring 10 that is rotatably held on the inner periphery of the frame; the opening/closing-type floor 20 which is provided inside the ring and of which a portion through which the irradiation device passes can be opened and closed; and drive means 28 that reversely rotates the ring in synchronization with the rotation of the irradiation device so as to maintain the opening/closing-type floor horizontal. Accordingly, it may be possible to obtain a rotating irradiation apparatus that can secure as large an access floor as possible, reduce noise during the formation of an access floor, and stably operate with a simple structure.

Since the rotating irradiation apparatus includes the slide opening/closing-type floor 20 and the opening/closing mechanism 9, it may be possible to solve problems where noise is generated during the drive of movable floors in the structure in the related art and manufacturing costs thereof are high.

If the slide opening/closing-type floor 20 and the opening/closing mechanism 9 are combined with the drive means that reversely rotates the opening/closing-type floor unit in synchronization with the rotation of the irradiation device 7, a cylinder mechanism for operating a rod in the related art is not needed and the movable floors do not need to be formed in the entire drive range of a particle beam irradiation unit. Accordingly, it may be possible to secure as large an access floor as possible with a simple structure.

In the first embodiment, there has been described a case where the invention is used for a particle radiation therapy apparatus. However, the subject of the invention is not limited thereto, and it is apparent that the invention may be applied to other radiation therapy apparatuses using X-rays or an electron beam likewise.

Second Embodiment

In the first embodiment, the opening/closing-type floor has been separated from the stationary floor surface. However, a receiving table of an opening/closing-type floor surface may be provided on the treatment table base that is a stationary floor. Accordingly, when the opening/closing-type floor is closed, one end floor surface may run on the receiving table. It may be possible to reduce the rigidity of the opening/closing-type floor by providing a stationary receiving table, and to reduce the manufacturing costs and weight of the opening/closing-type floor surface and a floor surface frame material.

Figure 4:
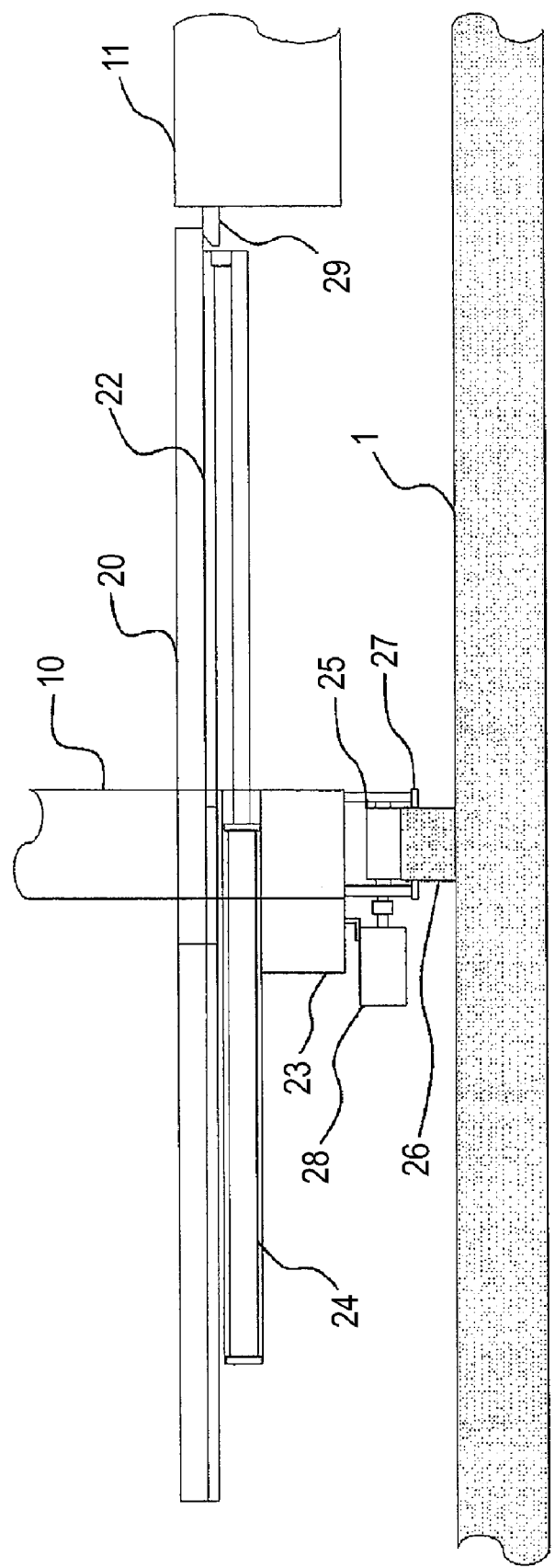
FIG. 4 is a side view showing the cross-section of a stationary floor and opening/closing-type floor according to a second embodiment of the invention.

FIG. 4 shows the structure of a movable floor and a stationary floor of a second embodiment. Reference numeral 29 in FIG. 4 denotes a receiving table provided at the treatment table base 11 that is a stationary floor.

In the second embodiment, when being closed, the opening/closing-type floor 20 runs on the stationary receiving table 29 or a small gap is formed. Accordingly, it may be possible to maintain the flexure of the opening/closing-type floor surface when a load is applied to the opening/closing-type floor surface. If the opening/closing-type floor 20 is formed so as to run on the stationary receiving table 29 when being closed, it may be possible to make the opening/closing-type floor easily run on the stationary receiving table by forming an end of the stationary receiving table 29 in a tapered shape. Since the load is supported by the stationary receiving table 29, the rigidity of the opening/closing-type floor may be lower than that of the opening/closing-type floor 20 of the first embodiment and it may be possible to reduce the manufacturing costs and weight of the opening/closing mechanism 9.

Even in the second embodiment, the opening/closing-type floor 20 is not fixed and connected to the stationary receiving table 29. That is, the opening/closing-type floor 20 is independent of the stationary receiving table 29. Accordingly, even though the angle of the ring 10 is slightly changed when the ring 10 is reversely rotated in synchronization with the rotation of the rotating gantry as described in the first embodiment, there is no concern that the opening/closing-type floor 20 is damaged.

Third Embodiment

In the first and second embodiments, the levelness of the ring 10 including the opening/closing mechanism 9 may be monitored, an interlock may be provided, and levelness monitoring sensors, such as photoelectric sensors and a pendulum-type inclination sensor, may be provided in order to secure safety.

Figure 5:
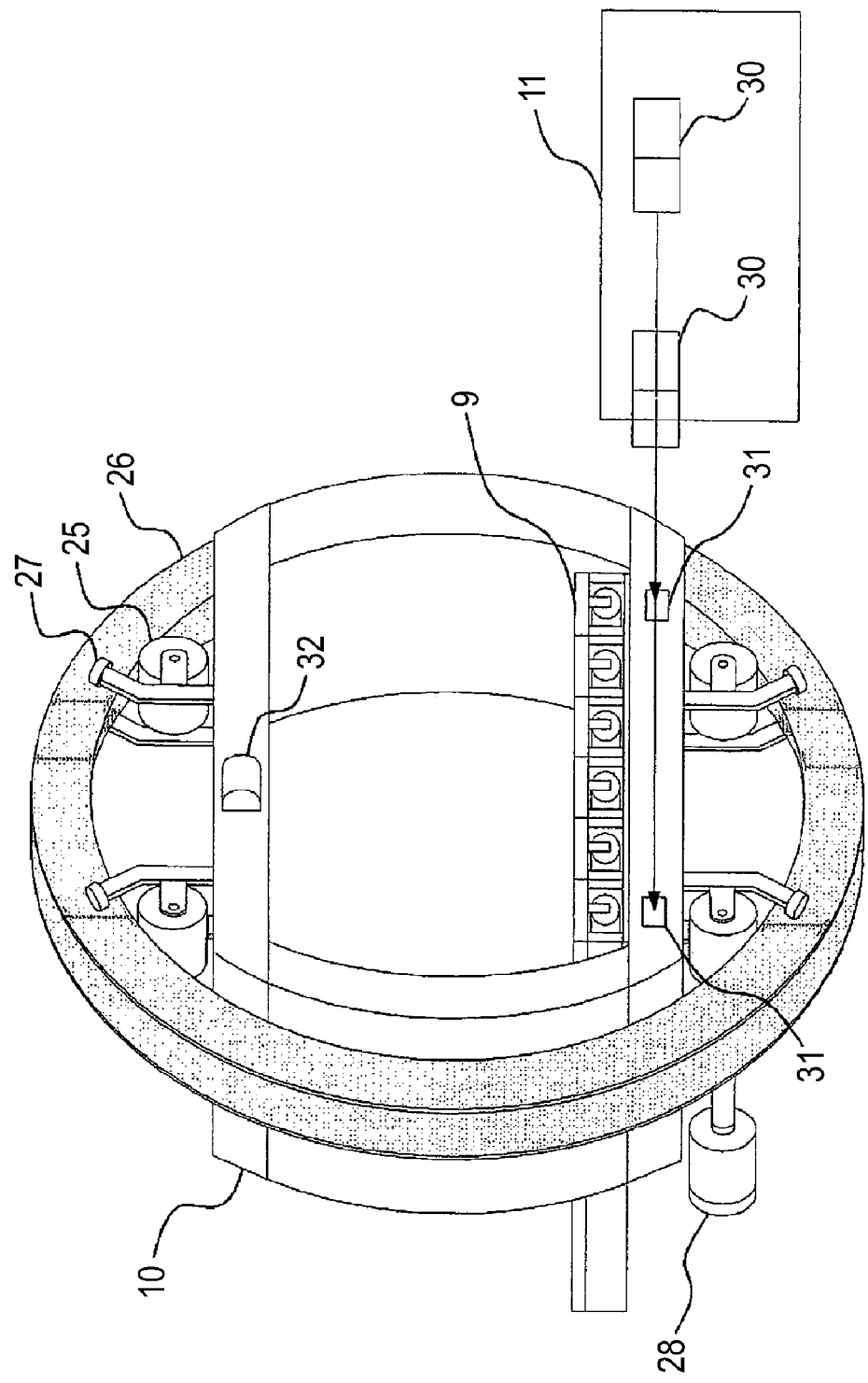
FIG. 5 is a schematic perspective view showing the main parts of a rotating irradiation apparatus according to a third embodiment of the invention.
Figure 6:
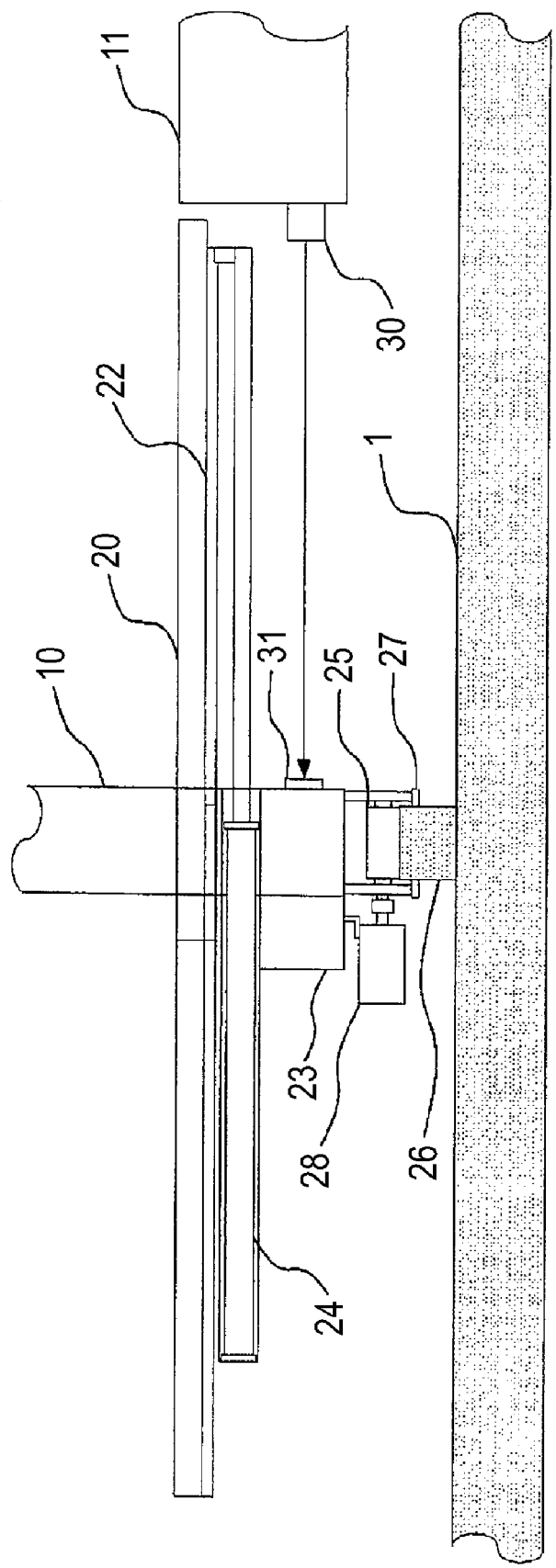
FIG. 6 is a side view of an opening/closing mechanism of an opening/closing-type floor according to the third embodiment of the invention.

FIGS. 5 and 6 show the structure where the two kinds of sensors are disposed. Reference numeral 30 denotes a photoelectric sensor, reference numeral 31 denotes a reflecting plate for the photoelectric sensor 30, and reference numeral 32 denotes a pendulum-type inclination sensor.

If the photoelectric sensors 30 are disposed on the treatment table base 11 and the reflecting plates 31 are disposed on the ring 10 as shown in FIGS. 5 and 6, it may be possible to detect whether the ring 10 is deviated from an allowable range relative to the treatment table base 11. When it is detected that the ring is deviated from an allowable range relative to the treatment table base, it may be possible to secure safety at the time of an abnormal operation by stopping the rotation of the gantry as a safety measure.

In the disposition shown in FIGS. 5 and 6, it is thought that incident light or reflected light of the photoelectric sensor 30 and the reflecting plates 31 is blocked by the irradiation device 7 at a certain rotation angle of the rotating gantry. However, it may be possible to solve the above-mentioned problem by disposing two or more sets of the photoelectric sensors 30 and the reflecting plates 31 at a sufficient angle. When an inclination angle is generated, a pendulum causes angular displacement. If the pendulum-type inclination sensor 32 for detecting this position displacement also has the same function, it may be possible to secure high safety. Since it is apparent that the same advantage is obtained even though a magnetic inclination sensor or the like is used other than the above-mentioned sensors, it may be possible to secure safety by using one or more of the above-mentioned sensors.

Fourth Embodiment

In the third embodiment, there has been described an example of the detection of a case where the opening/closing mechanism 9 is deviated from allowable levelness when the opening/closing mechanism 9 is reversely rotated in synchronization with the rotating gantry. However, as the fourth embodiment, there will be described a countermeasure against a worst case where the opening/closing-type floor 20 of the opening/closing mechanism 9 causes an abnormal operation and the opening/closing-type floor 20 and the irradiation device 7 interfere with each other in the first and second embodiments.

Figure 7:
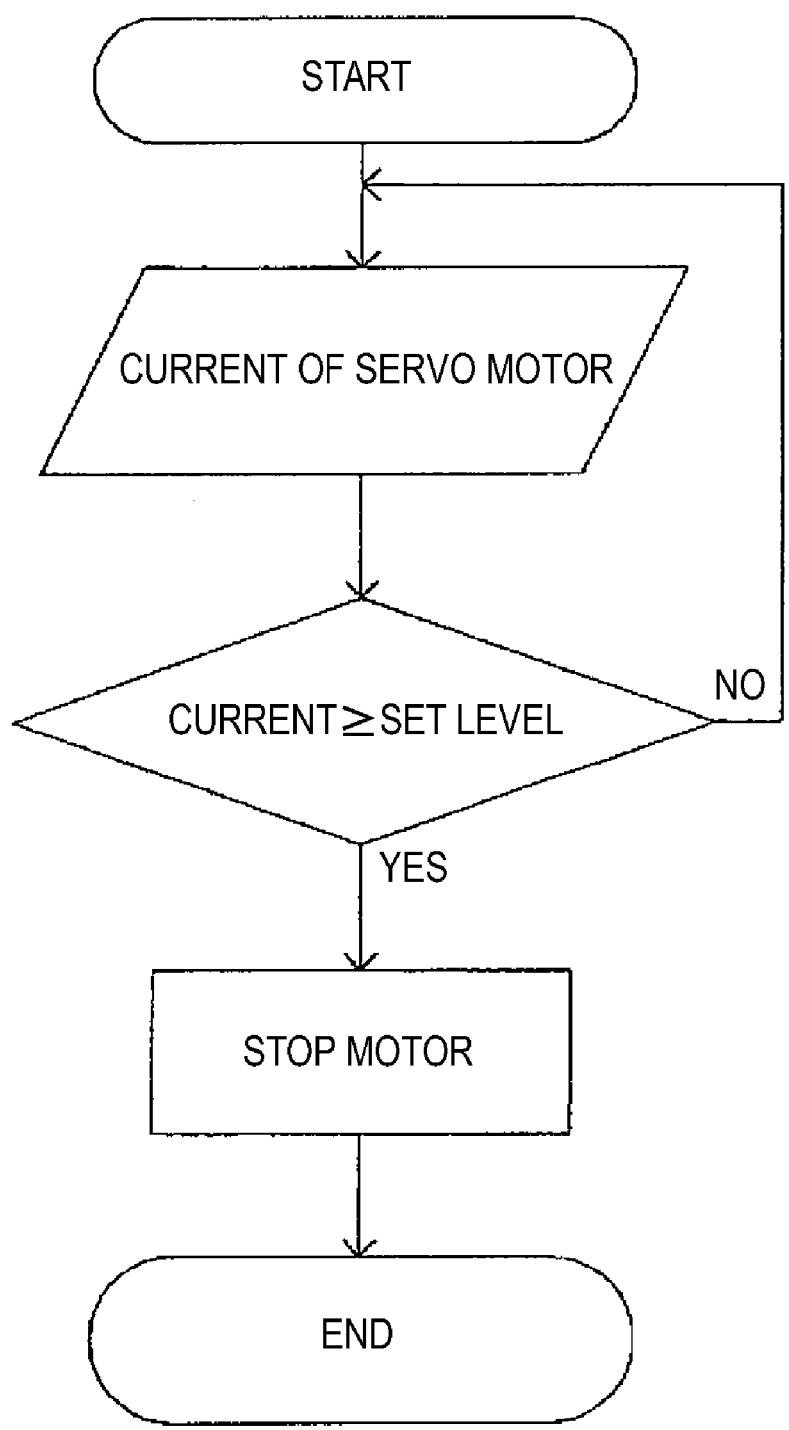
FIG. 7 is a flowchart illustrating a method of controlling a drive motor according to a fourth embodiment of the invention.

If the irradiation device 7 is rotated to the floor unit while floors of the opening/closing-type floor 20, which should be opened, are closed, the drive motor 28 for maintaining the opening/closing mechanism 9 horizontal is controlled so as to be reversely rotated relative to the irradiation device 7. It is expected that the damage caused by interference between the irradiation device 7 and the opening/closing-type floor 20 becomes serious. Accordingly, as shown in a flowchart of FIG. 7, a load current limit is provided at the drive motor 28 of the ring 10 and the drive motor of the gantry drive device 3, it may be possible to detect that drive current becomes equal to or larger than a set level due to a load larger than the load during usual rotation, and it may be possible to reduce the damage to the device to the minimum by stopping the operation of the motor. It may be possible to secure high safety through the addition of the function of the third embodiment.

Fifth Embodiment

In the first and second embodiments, it may be possible to prevent the angular displacement of the ring 10 during the stop of the rotating gantry by disposing pneumatic or electric pushing means, which prevents angular displacement, below the ring 10 so that the ring 10 and the opening/closing mechanism 9 do not cause angular displacement relative to the guide ring 26 at the time of the stop of the rotating gantry.

Figure 8:
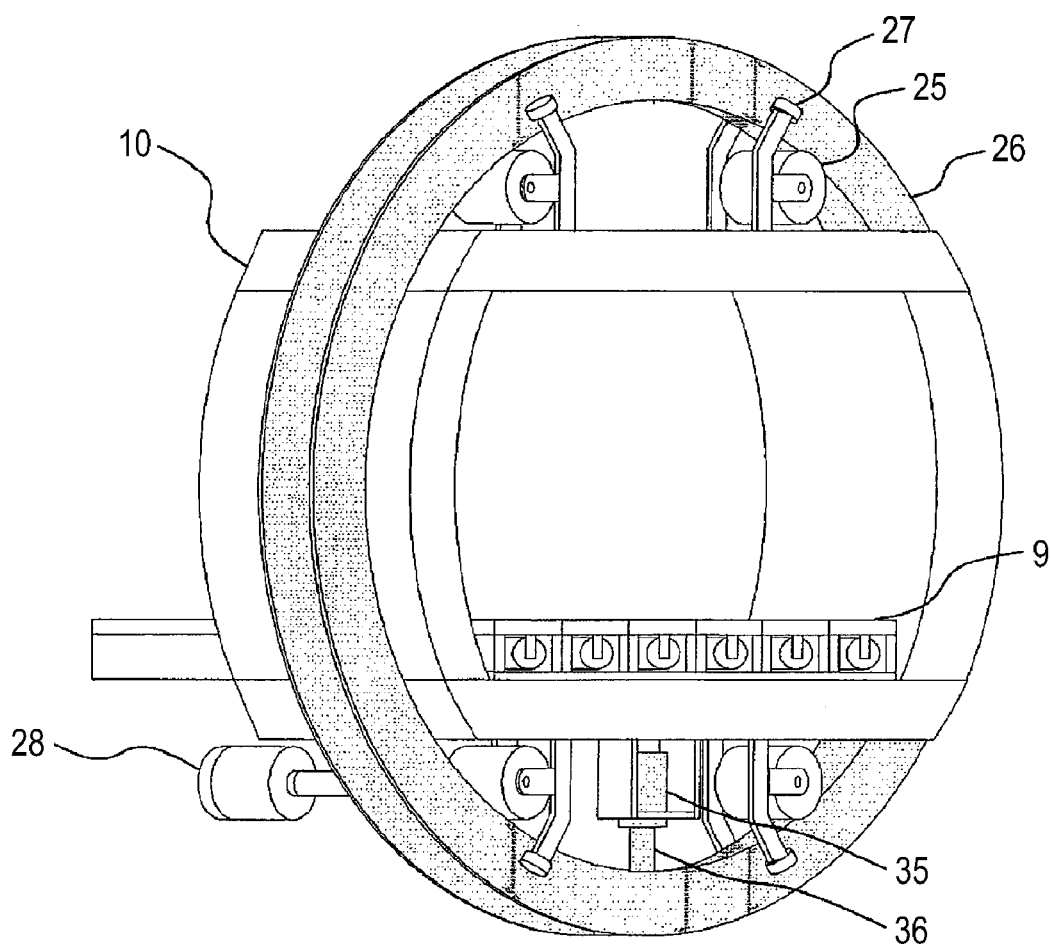
FIG. 8 is a schematic perspective view showing the main parts of a rotating irradiation apparatus according to a fifth embodiment of the invention.

In FIG. 8, reference numeral 35 denotes a pushing cylinder, reference numeral 36 denotes a pushing rod that prevents the angular displacement of the ring 10 relative to the guide ring 26 by being inserted and withdrawn by the pushing cylinder 35 and pushed against the guide ring 26.

If the pushing rod 36 is pushed against the guide ring 26 while being inserted at the time of the stop of the rotating gantry, the pushing rod 36 functions as a brake and can prevent angular displacement relative to the guide ring 26 of the ring 10. When the rotating gantry is operated, the pushing rod 36 is withdrawn and the ring 10 is reversely rotated in synchronization with the rotating gantry. It may be possible to secure higher safety by disposing pushing cylinder 35 and the pushing rod 36 below the ring 10 as described above.

Sixth Embodiment

The ring 10, which includes the opening/closing mechanism 9, is guided by the guide roller 26, and is reversely rotated in synchronization with the rotating gantry, has been formed in a circular shape in the first and second embodiments. However, even though the ring is formed in other shapes, the ring can have the same function.

Figure 9:
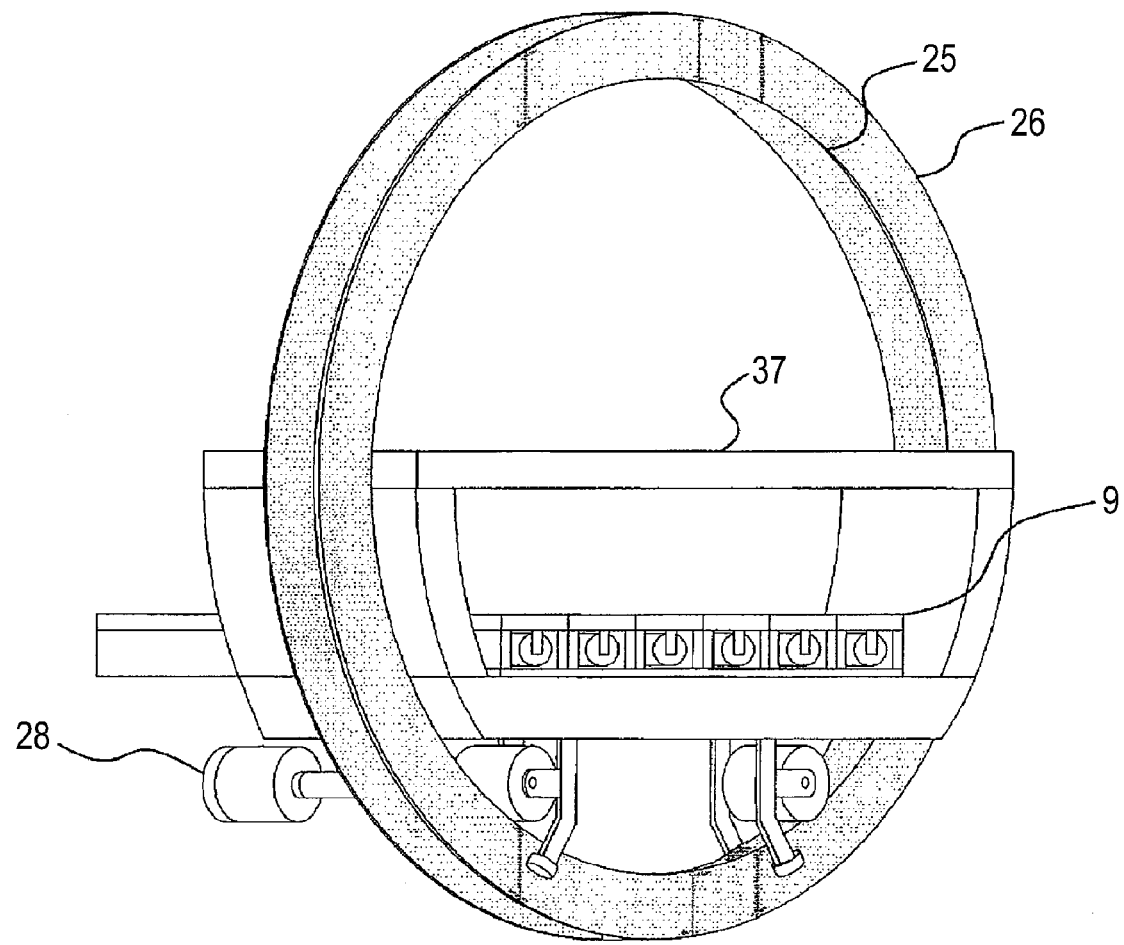
FIG. 9 is a schematic perspective view showing the main parts of a rotating irradiation apparatus according to a sixth embodiment of the invention.
Figure 10:
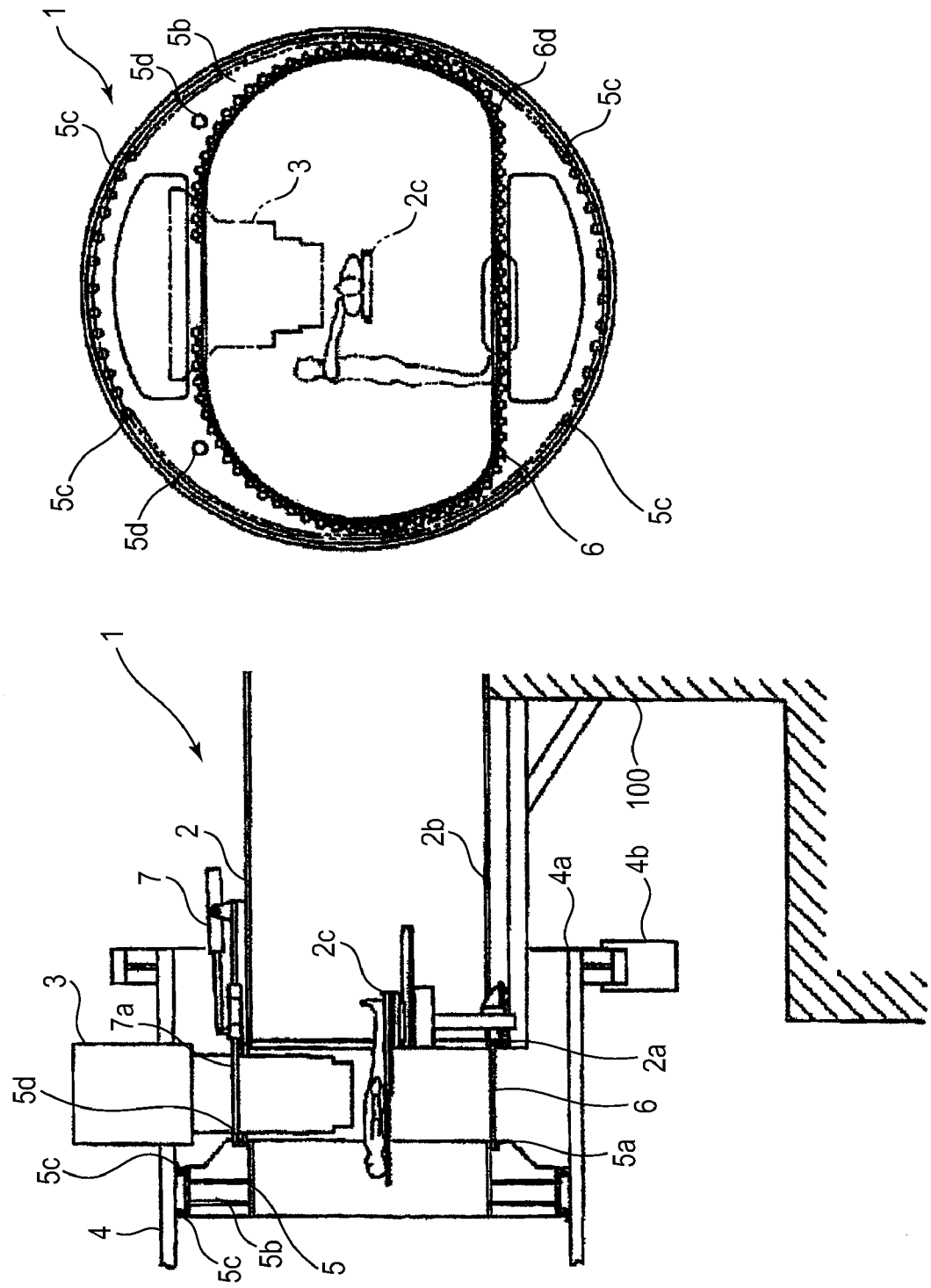
FIG. 10 is a cross-sectional view showing the main parts of a rotating irradiation chamber for particle radiation therapy in the related art.

In FIG. 9, reference numeral 37 denotes the semicircular ring 10. It is expected that the semicircular ring is inferior to the ring 10 of the first embodiment in terms of rotational stability. However, if the ring 10 is formed in a semicircular shape in this embodiment, it may be possible to obtain advantages of reducing the weight of the rotating gantry and to reduce the material cost of the rotating gantry. Of course, it is apparent that the ring can have the same function even though the ring 10 is formed in other shapes other than for the semicircular shape. Accordingly, cases where the ring is formed in other shapes other than for the ring and has the same function as described above are included in this embodiment.

The invention claimed is:

1. A rotating irradiation apparatus comprising:
   an irradiation device that irradiates a charged particle beam;
   a frame on which the irradiation device is mounted and which rotates the irradiation device so that a patient lying on a treatment table fixed to a stationary floor surface is irradiated with the charged particle beam;
   a ring that is rotatably held on an inner periphery of the frame;
   an opening/closing-type floor which is provided inside the ring and of which a portion through which the irradiation device passes is openable and closable; and
   a drive motor that reversely rotates the ring in synchronization with the rotation of the irradiation device, and is controlled by feedback so as to maintain the horizontal opening/closing-type floor,
   wherein the opening/closing-type floor is formed of a plurality of segmented slide floors, wherein portions of the opening/closing-type floor are slidable relative to other portions of the opening/closing-type floor and the opening/closing-type floor forms an access floor only in the frame without being connected to the stationary floor surface when being closed.

2. The rotating irradiation apparatus according to claim 1, further comprising:
   a receiving table provided on the stationary floor surface so as to form a gap under one end of the opening/closing-type floor when the opening/closing-type floor is closed.

3. The rotating irradiation apparatus according to claim 1, further comprising:
   an inclination sensor that measures the levelness of the ring.

4. The rotating irradiation apparatus according to claim 1, wherein the drive motor is stopped when drive current having a value equal to or higher than a predetermined value flows in the drive motor.

5. The rotating irradiation apparatus according to claim 1, further comprising:
   pushing means disposed in the ring for preventing angular displacement of the frame and the ring during the stop of the irradiation device.

6. The rotating irradiation apparatus according to claim 1, wherein the ring has a semicircular shape.

* * * * *